United States Patent
Morris et al.

(10) Patent No.: US 9,610,423 B2
(45) Date of Patent: Apr. 4, 2017

(54) SLEEVE VALVE CATHETERS

(75) Inventors: Mary M. Morris, Shoreview, MN (US); Timothy G. Laske, Shoreview, MN (US); Kenneth T. Heruth, Edina, MN (US); Michael R. Ujhelyi, Maple Grove, MN (US); Jesus W. Casas, Brookylyn Park, MN (US); David S. Olson, Scandia, MN (US)

(73) Assignee: Medtronic, Inc., Minneapolis, MN (US)

( * ) Notice: Subject to any disclaimer, the term of this patent is extended or adjusted under 35 U.S.C. 154(b) by 935 days.

(21) Appl. No.: 13/486,523

(22) Filed: Jun. 1, 2012

(65) Prior Publication Data

US 2012/0245533 A1 Sep. 27, 2012

Related U.S. Application Data

(63) Continuation of application No. 11/754,759, filed on May 29, 2007, now abandoned, which is a continuation-in-part of application No. 10/382,757, filed on Mar. 6, 2003, now Pat. No. 7,235,067.

(51) Int. Cl.
*A61M 1/00* (2006.01)
*A61M 25/00* (2006.01)

(52) U.S. Cl.
CPC .............................. *A61M 25/0075* (2013.01)

(58) Field of Classification Search
CPC ...... A61M 25/0075; A61M 2025/0076; A61M 2039/0666; A61M 2039/2433; A61M 2039/244

USPC ...... 604/537, 246, 9, 118, 247, 48, 604/99.01–99.04, 96.01, 101.01, 101.02, 604/103.05, 171, 172, 264, 523
See application file for complete search history.

(56) References Cited

U.S. PATENT DOCUMENTS

| | | | |
|---|---|---|---|
| 2,050,407 A | 4/1935 | Wolff | |
| 3,726,283 A * | 4/1973 | Dye et al. | 604/99.03 |
| 3,812,860 A | 5/1974 | Gilbert et al. | |
| 3,833,003 A | 9/1974 | Taricco | |
| 4,100,923 A | 7/1978 | Southern | |
| 4,657,536 A | 4/1987 | Dorman | |
| 5,112,301 A | 5/1992 | Fenton, Jr. et al. | |
| 5,147,332 A | 9/1992 | Moorehead | |
| 5,484,425 A | 1/1996 | Fischell et al. | |
| 5,690,682 A | 11/1997 | Buscemi et al. | |
| 5,728,066 A | 3/1998 | Daneshvar | |
| 5,738,663 A * | 4/1998 | Lopez | 604/249 |
| 5,800,498 A | 9/1998 | Obino et al. | |
| 6,783,522 B2 | 8/2004 | Fischell | |
| 7,235,067 B2 | 6/2007 | Morris et al. | |
| 7,351,214 B2 * | 4/2008 | Burgermeister | 600/585 |
| 2003/0216710 A1 | 11/2003 | Hurt | |
| 2004/0049169 A1 * | 3/2004 | Fischell | 604/537 |

* cited by examiner

*Primary Examiner* — Emily Schmidt
(74) *Attorney, Agent, or Firm* — Carol F. Barry

(57) ABSTRACT

A catheter body includes an exit port over which a pressure responsive sleeve is formed that allows material to exit a lumen of the catheter body at a given pressure. In one embodiment, a surface of the sleeve is approximately flush with a surface of the catheter body.

9 Claims, 12 Drawing Sheets

SLEEVE VALVE CATHETERS

RELATED APPLICATION

This application is a continuation of U.S. patent application Ser. No. 11/754,759, filed May 29, 2007 entitled "SLEEVE VALVE CATHETERS" which is a continuation-in-part to non-provisional U.S. patent application Ser. No. 10/382,757 filed Mar. 6, 2003, U.S. Pat. No. 7,235,067, herein incorporated by reference in its entirety.

This application is related to U.S. patent application Ser. No. 13/486,611, filed on even date herewith entitled "SLEEVE VALVE CATHETERS" herein incorporated by reference in its entirety.

TECHNICAL FIELD

The invention relates to sleeve valve catheters for administration of material into a body of a patient.

BACKGROUND

Medical catheters are used for the administration of therapeutic agents or nutrients either into a blood stream or a body cavity of a patient. A catheter includes an exit port to deliver solutions, for example nutrients or therapeutic agents, or a combination thereof, from a lumen of the catheter to the body.

Conventional catheters include at least one pressure responsive valve, such as a sleeve valve. A sleeve valve is formed by covering an exit port of the catheter with a sleeve. The sleeve is constructed of an elastic material to provide the sleeve with the ability to expand and contract in response to pressure gradients. The pressure responsive valve opens and, in turn, permits fluid flow through the catheter in response to an applied pressure differential. More particularly, when the pressure differential exceeds a threshold, the fluid in the lumen of the catheter expands the sleeve and flows out of the catheter. When the pressure differential decreases below the threshold pressure differential, the sleeve forms a seal with the exterior of the catheter to prevent fluid flow in or out of the catheter.

Some patients may require an implanted catheter for an extended period of time. However, catheters that remain implanted in a body of a patient may become occluded over time due to blood ingression, thrombus formation or fibrous tissue encapsulation. When a catheter does become occluded, the patient will not receive the necessary therapeutic agents or nutrients. In this case, the catheter must be removed and either cleaned or replaced with a new catheter.

DETAILED DESCRIPTION

Figure 1:
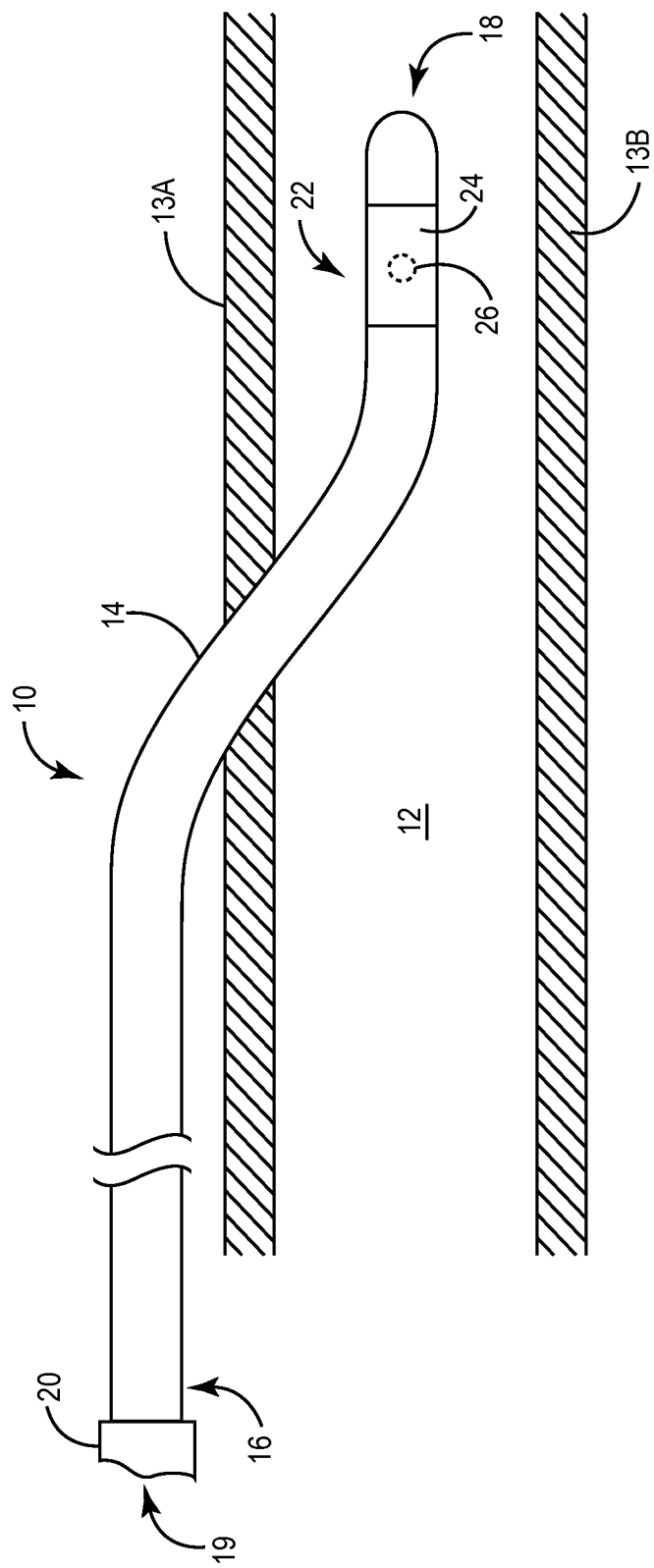
FIG. 1 is a schematic diagram illustrating a sleeve valve catheter.

FIG. 1 is a schematic diagram illustrating a sleeve valve catheter 10 for administration of therapeutic agents or nutrients into a body of a patient. Sleeve valve catheter 10 is inserted into the body of the patient and, more particularly, into a vessel 12 of the patient defined by vessel walls 13A and 13B ("vessel walls 13"). Sleeve valve catheter 10 infuses fluid or other material into the blood stream flowing through vessel 12. Although in the example of FIG. 1 sleeve valve catheter 10 is implanted within vessel 12, sleeve valve catheter 10 may be implanted in other body lumens, cavities, or spaces, such as the brain ventricle.

In the example of FIG. 1, sleeve valve catheter 10 includes a catheter body 14 with a proximal end 16 that resides outside of the body of the patient and a distal end 18 that is implanted within vessel 12. In other embodiments, proximal end 16 may be within the body and coupled to an implanted drug delivery device or a catheter access port. Sleeve valve catheter 10 receives a fluid or other material via an opening 19 at proximal end 16. The fluid, for example, may be a solution that includes therapeutic agents, nutrients, or a combination thereof to be delivered to the body of the patient. Therapeutic agents include, for example, drugs, cells, proteins, and genetic material. As illustrated in FIG. 1, proximal end 16 includes a fitting 20 that couples to a source of the fluid or to a device that injects the fluid into the body of the patient. Types of fitting 20 include a quick-connect fitting and a luer lock fitting, and types of material sources include a syringe, a pump, and other similar injection devices.

Distal end 18 of catheter body 14 may be tapered to reduce the likelihood of thrombus formation at distal end 18. Thrombus formation generally occurs in regions of turbulence and/or stagnancy in the blood flow, which leads to clotting. In the example of FIG. 1, the distal end of catheter body 14 is rounded to reduce the amount of blood flow turbulence and stagnancy. However, distal end 18 may be tapered differently. For instance, distal end 18 may have a linear or nonlinear taper. Catheter body 14 may be closed at distal end 18 in order to build up pressure within catheter body 14 to open a pressure responsive valve.

Sleeve valve catheter 10 further includes at least one sleeve valve 22 that functions as a one-way pressure responsive valve. In other words, sleeve valve 22 permits fluid flow from catheter 10 to vessel 12, but restricts fluid flow into catheter 10. Sleeve valve 22 comprises a sleeve 24 that surrounds a portion of catheter body 14 proximate an exit port 26 and covers exit port 26. Sleeve 24 is constructed of an elastic material, which provides sleeve 24 the ability to expand and contract. When fluid within a lumen formed by catheter body 14 generates a large pressure differential between inside catheter body 14 and outside catheter body 14, the fluid in the lumen attempts to exit catheter body 14 via exit port 26.

In response to the pressure build-up within catheter body 14, sleeve 24 expands. With a large enough pressure differential, sleeve 24 will expand enough to allow the fluid to flow from catheter body 14 to vessel 12. In this manner, sleeve valve catheter 10 administers therapeutic agents or nutrients into a body of a patient. When the fluid within the lumen of catheter body 14 does not have a high pressure level, sleeve 24 forms a seal with an exterior surface of catheter body 14, preventing fluid from flowing into or out of catheter body 14.

In one embodiment, sleeve valve catheter 10 includes a plurality of sleeve valves. One or more sleeve valves act as surrogate valves in the case a primary valve becomes occluded. The plurality of sleeve valves may be longitudinally displaced relative to one another along a length of catheter body 14.

Figure 9A:
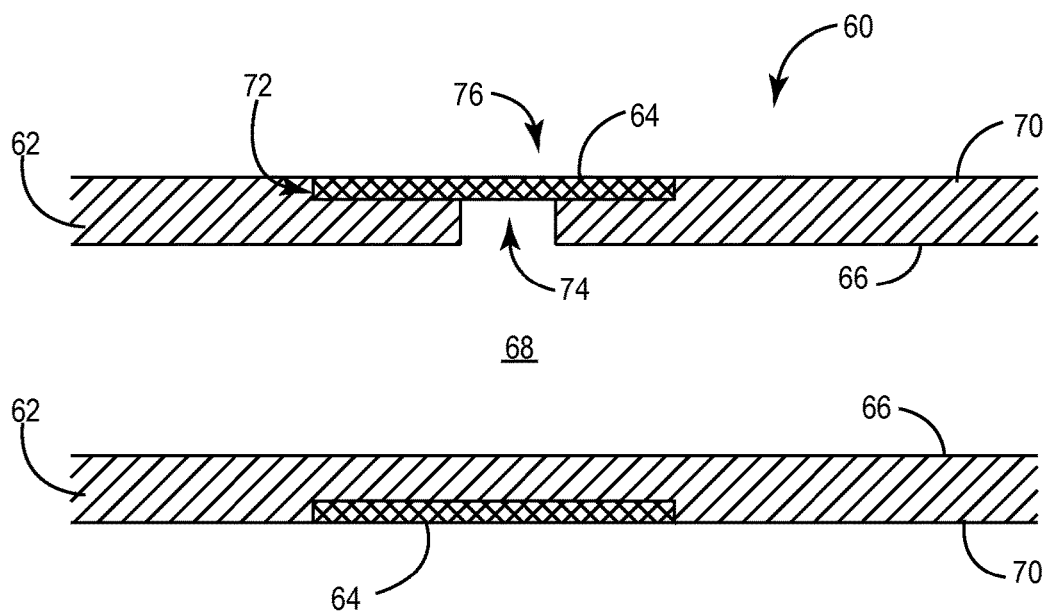
FIG. 9 is a cross-sectional side view illustrating an exemplary sleeve valve catheter that includes a sleeve having substantially the same outer diameter as a catheter body that the sleeve surrounds.
Figure 9B:
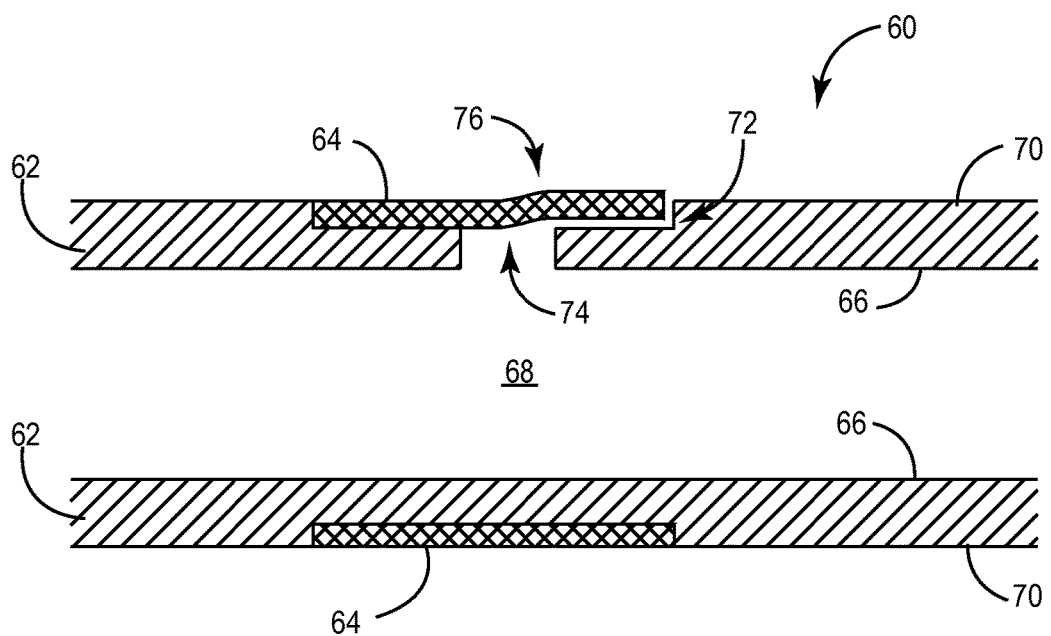

In accordance with one embodiment of the invention, as in the example illustrated in FIG. 1, catheter body 14 includes a recess that receives sleeve 24 such that sleeve 24 has substantially the same outer diameter as catheter body 14. In this manner, an exterior surface of sleeve 24 is substantially flush with the exterior surface of catheter body 14, which reduces the turbulence and/or stagnancy in the blood flow adjacent the edge of sleeve 24 that may lead to thrombus formation. FIGS. 9A-B and 10 further describe alternate embodiments of such sleeve valve catheters. In other embodiments, if sleeve 24 is not positioned within a recess, one or both edges of sleeve 24 are tapered to reduce the turbulence and/or stagnancy in the blood flow adjacent the edge of sleeve 24.

In another embodiment of the present invention, an exterior portion of sleeve valve catheter 10 includes a coating that elutes a therapeutic agent. The coating may be on an exterior portion of sleeve 24, an exterior portion of catheter body 14, or both. According to various embodiments, agents eluted from the coating are selected from a group including drugs, proteins, and genes adapted to reduce the likelihood of thrombus formation or fibrous tissue encapsulation. For example, the exterior portion of sleeve valve catheter 10 includes a coating of Heparin to reduce the likelihood of thrombus formation.

Sleeve 24 is constructed of an elastic material such as silicone. The elastic material gives sleeve 24 the compliance to expand and contract in response to applied pressure differentials. Catheter body 14 is constructed such that sleeve 24 is more compliant than catheter body 14. Sleeve 24 must be more compliant than catheter body 14 in order for the applied pressure differentials to open sleeve valve 22. In one embodiment according to the present invention, catheter body 14 is constructed of a non-compliant polymer to prevent catheter body 14 from expanding, or 'ballooning', which increases the liquid volume and pressure necessary to open sleeve valve 22. Non-compliant polymers, from which catheter body 14 is constructed, are selected from a group of biocompatible materials including polyurethane, fluoropolymers, polyimide, polyamide, polyethylene, and polypropylene. In another embodiment according to the present invention catheter body 14 is constructed of a compliant material such as a silicone, wherein walls of catheter body 14 are formed thicker than sleeve 24 so that catheter body 14 is less compliant than sleeve 24. When sleeve 24 and catheter body 14 are both constructed of silicone, crosslinking between the silicone material of sleeve 24 with the silicone material of catheter tube 14 may cause sleeve 24 and catheter body 14 to stick together and resist opening in response to the pressure differential. According to another embodiment of the present invention, in which both catheter body 14 and sleeve 30 are constructed of silicone, a material is applied at the interface between sleeve 24 and body 14 in order to prevent blocking between the interface of catheter body 14 and sleeve 30. The term "blocking" refers to the cross-linking between the silicone material of sleeve 30 with the silicone material of catheter tube 14.

Sleeve valve catheter 10 performs as any of a number of catheters for administration of therapeutic agents or nutrients into a body of a patient, for example, a central venous catheter, a vascular catheter, an intra-cerebral ventricular catheter, a pericardial catheter, an intrathecal catheter, or an epidural catheter. The different catheters may vary in size and shape depending on the application; for example, a catheter that is placed in a smaller vessel needs to have a smaller diameter than a catheter that is placed in a larger vessel.

Figure 2A:
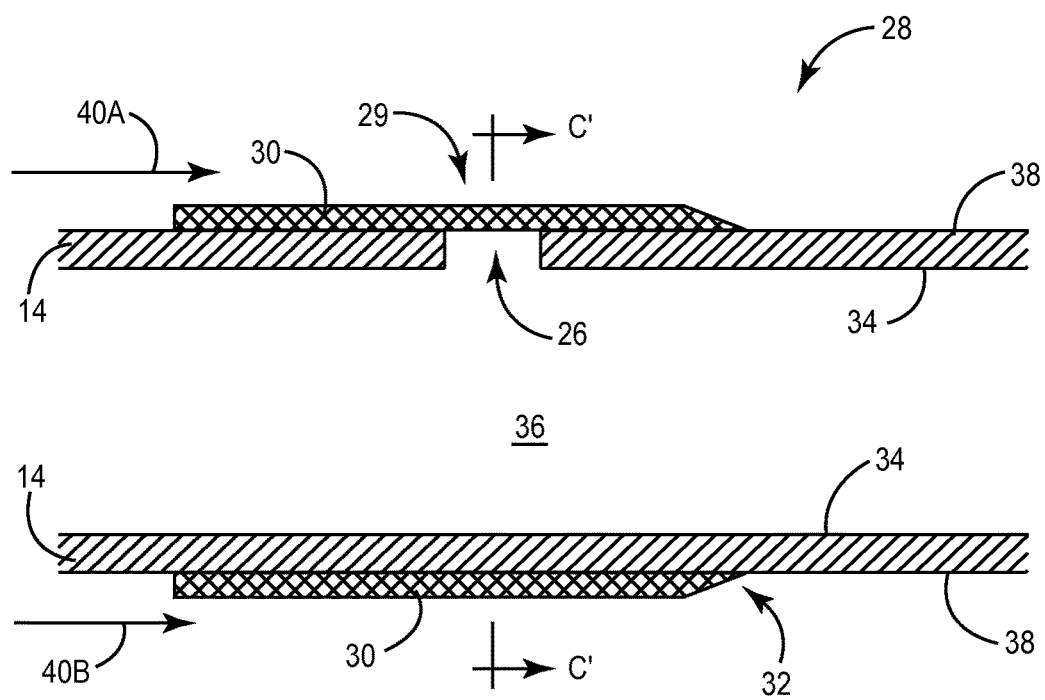
FIG. 2 is a cross-sectional side view illustrating an exemplary sleeve valve catheter that comprises a sleeve with a tapered edge.
Figure 2B:
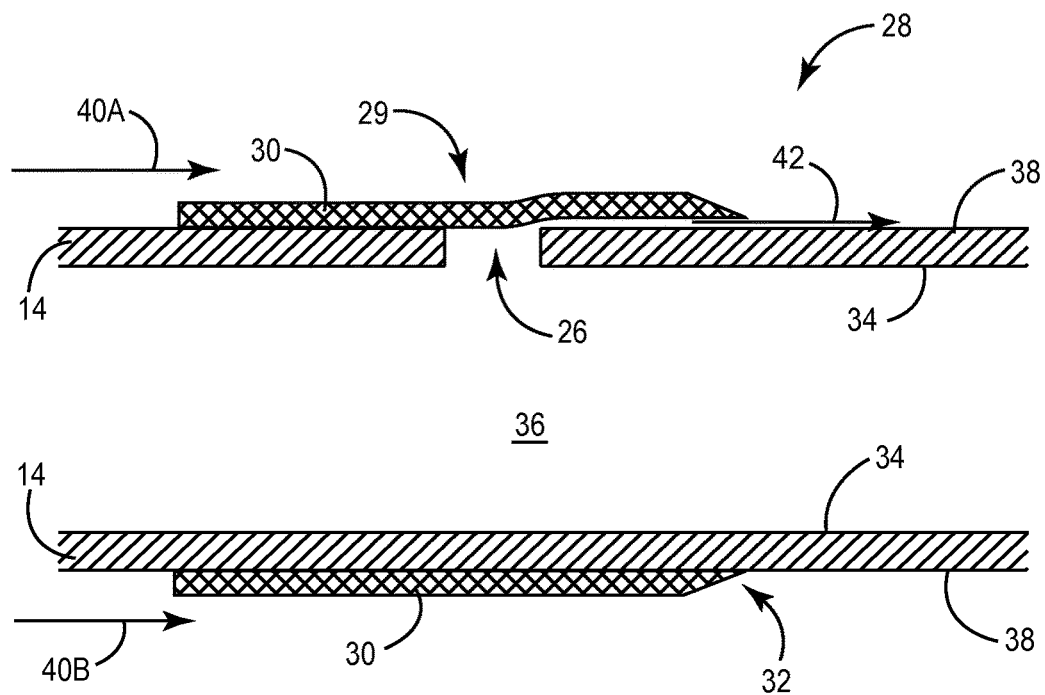

FIG. 2 is a cross-sectional side view of an exemplary sleeve valve catheter 28 that comprises a sleeve 30 with a tapered edge 32 to reduce the likelihood of occlusion. FIG. 2(A) illustrates sleeve valve catheter 28 in a closed state. The term "closed" state refers to a state in which a large enough pressure differential does not exist to open sleeve valve catheter 28 to allow fluid flow from the interior lumen of sleeve valve catheter 28 to a body of a patient. FIG. 2(B) illustrates sleeve valve catheter 28 in an open state. The term "open" state refers to a state in which a large enough pressure differential exists to overcome the elastic force of sleeve 30 and thereby open sleeve valve catheter 28, allowing the sleeve valve catheter to infuse fluid into the body of the patient.

Sleeve valve catheter 28 comprises a catheter body 14 including an interior surface 34 defining a lumen 36 and an exterior surface 38 exposed to an environment within a vessel 12. Sleeve valve catheter 28 further includes at least one exit port 26 along catheter body 14 through which material exits lumen 34. Sleeve 30 surrounds a portion of exterior surface 38 and covers exit port 26. In one embodiment according to the present invention, an inner diameter of sleeve 30 is substantially equal to an outer diameter of catheter body 14 such that sleeve 30 fits snuggly around the portion of exterior surface 38 adjacent exit port 26. In other embodiments, the inner diameter of sleeve 30 is slightly smaller than the outer diameter of catheter body 14 in order to create a tighter fit. In alternate embodiments, exit port 26 is circular, oval, square or any other geometric shape. Sleeve 30 and exit port 26 together form pressure responsive sleeve valve 29.

Blood flow over sleeve 30 occurs in the direction indicated by arrows 40A and 40B ("arrows 40"). In the example of FIG. 2(A), sleeve valve catheter 28 is in a closed state. While in the closed state, sleeve 30 forms a seal with the portion of exterior surface 38 adjacent exit port 26 to prevent fluid flow from lumen 36 to the body of the patient. In one embodiment, tapered edge 32 is proximate distal end 18 of catheter 28. Alternatively, tapered edge 32 is farther from distal end 18, or both edges of sleeve 30 are tapered to further reduce turbulence and stagnancy in the blood flow.

In one embodiment according to the present invention, sleeve 30 is molded, via Liquid Silicone Rubber (LSR) molding techniques, often referred to as Liquid Injection Molding (LIM), to form tapered edge 32; a material from which sleeve 30 is molded, liquid silicone rubber, or LSR, allows molding of sleeve 30 with a thickness and uniformity that is not possible with conventional silicone molding techniques. According to one embodiment, the LSR used to mold sleeve 30 is selected to have a lower viscosity than the conventionally used high consistency rubber (HCR) silicone, also known as gum stock silicone. The lower viscosity of the LSR improves flowability and helps to achieve a reduced thickness of sleeve 30, which increases the compliance and lowers the opening pressure of sleeve 30. Conventional molding techniques, such as hot silicone molding, for example, achieve a sleeve thickness of approximately 0.010 inches. Using LSR, however, the sleeve thickness may be reduced to nearly 0.0025 inches. LSR molding may be performed using standard thermo-set injection molding machines that have an LSR conversion kit installed. These molding machines may be obtained from vendors such as Boy, Engel, or Arburg.

Further, LSR allows tapered edge 32 to be molded rather than cut. However, according to another embodiment of the present invention, sleeve 30 is formed using other shaping techniques such as hot or cold transfer silicone molding, injection molding, extrusion, dipping or the like. For example, sleeve 30 is extruded and then cut to form tapered edge 32.

Tapered edge 32 has a constant negative slope that gradually tapers from an outer edge of sleeve 30 to exterior surface 38 of catheter body 14. The slope of tapered edge 32 may be varied to achieve a more gradual taper or a steeper taper.

In the example of FIG. 2(B), sleeve valve catheter 28 is in an open state. Sleeve valve catheter 28 transforms from the closed state to the open state in response to an increased pressure level within lumen 36 that causes sleeve valve 29 to open. More particularly, as the pressure level of a fluid within lumen 36 increases, the fluid attempts to exit lumen 36 via exit port 26. As the pressure of the fluid attempting to exit lumen 36 via exit port 26 increases, sleeve 30 begins to expand. Sleeve 30 continues to expand, in turn, breaking the seal between sleeve 30 and the portion of the exterior surface 38 adjacent exit port 26.

As illustrated in FIG. 2(B), the seal between sleeve 30 and exterior surface 38 breaks toward one of the edges of sleeve 30. However, seal between sleeve 30 and exterior surface 38 may be broken toward both edges of sleeve 30 in other embodiments. When the pressure differential between inside catheter body 14 and outside catheter body 14 is large enough, sleeve 30 will expand enough to put lumen 36 in fluid communication with the blood flow through vessel 12. The pressure differential is such that sleeve valve catheter 28 infuses nutrients or therapeutic agents into the body of the patient as shown by arrow 42. Further, the large pressure differential when the valve is open generally prevents the occurrence of blood ingression into lumen 36 during the open state.

The pressure level at which sleeve 30 expands depends on the properties of sleeve 30 such as the compliance of sleeve 30, the length of sleeve 30, the thickness of sleeve 30 or any combination thereof. For example, a thickness of sleeve 30 near distal end 18 is thinner than a thickness of sleeve 30 toward proximal end 16 so that sleeve 30 only opens toward distal end 18. The pressure differential at which sleeve 30 expands may further depend on the size and shape of exit port 26. For example, a larger exit port needs a smaller pressure differential to cause sleeve 30 to expand than a smaller exit port.

As described above, sleeve 30 is constructed of an elastic material such as silicone and must be more compliant than catheter body 14 in order for sleeve valve 29 to operate properly. In the case in which both catheter body 14 and sleeve 30 are constructed of silicone, according to one embodiment of the present invention, a material, for example graphite or talc, is applied at the interface between sleeve 30 and body 14 in order to prevent blocking between body 14 and sleeve 30. The term "blocking" refers to the crosslinking between the silicone material of sleeve 30 with the silicone material of catheter tube 14, which can cause sleeve 30 and catheter tube 14 to stick together and resist opening in response to the pressure differential. Crosslinking between the interface of catheter body 14 and sleeve 30 occurs at a given time and temperature. When blocking occurs, a much higher pressure differential is needed to open sleeve valve 30, which is undesirable.

Figure 3:
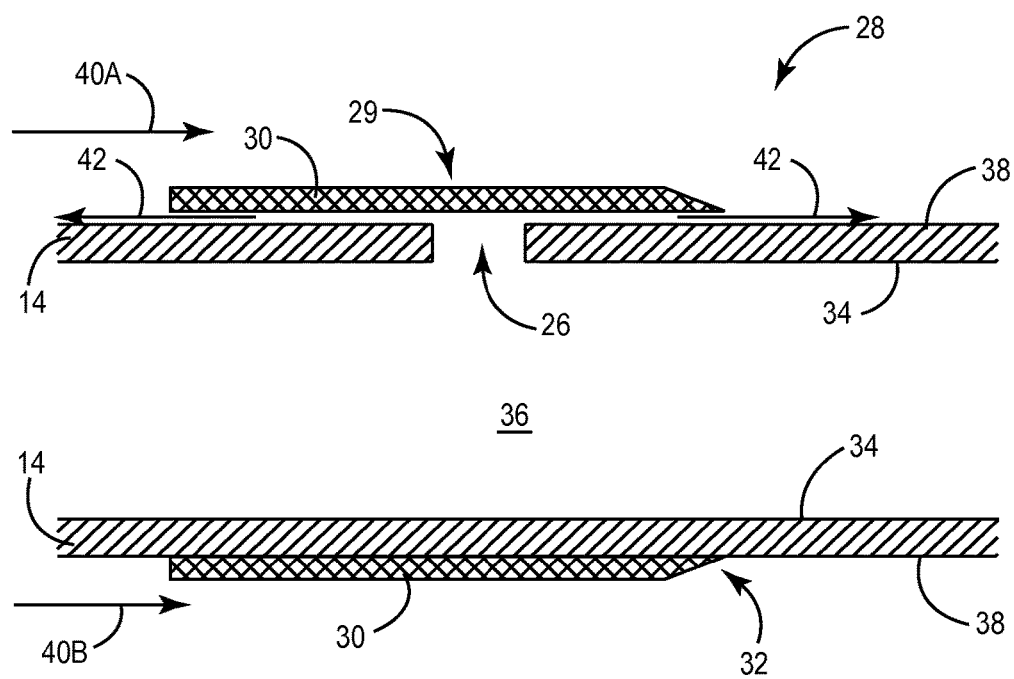
FIG. 3 is a cross-sectional side view of another exemplary sleeve valve catheter.

FIG. 3 is a cross-sectional side view of another exemplary sleeve valve catheter 43 that allows material to exit lumen 36 out both ends of sleeve 30. Sleeve valve catheter 43 conforms substantially to sleeve valve catheter 28 illustrated in FIG. 2(B), but the seal between sleeve 30 and exterior surface 38 breaks toward both edges of sleeve 30. In this manner, material exits lumen 36 via both ends of sleeve 30 as illustrated by arrows 42A-42B ("arrows 42").

Figure 4:
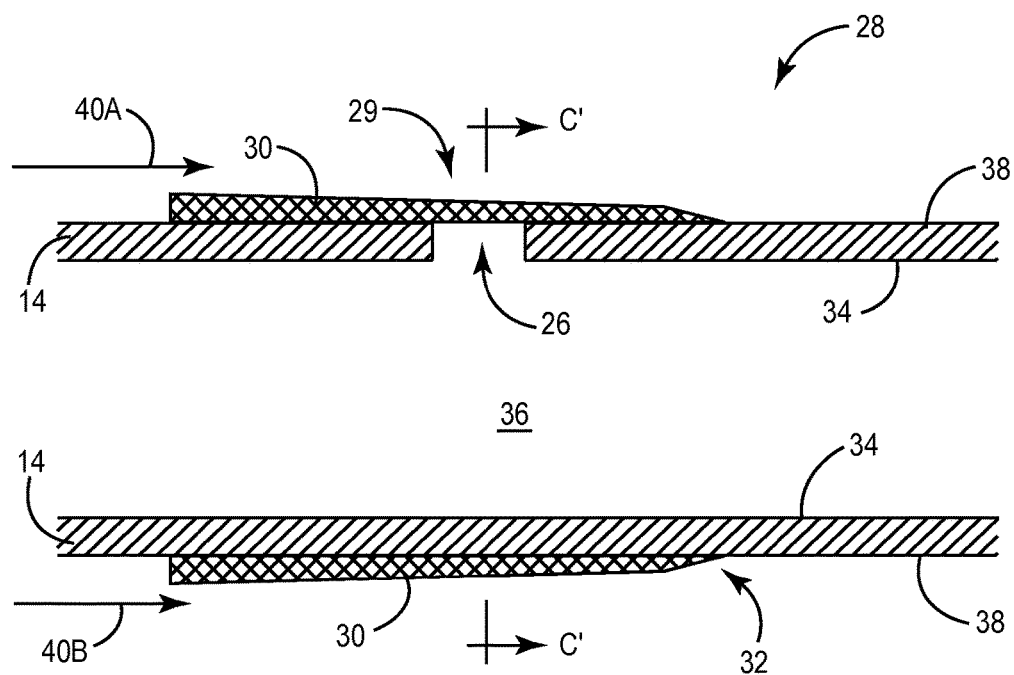
FIG. 4 is a cross-sectional side view of another exemplary sleeve valve catheter that has a non-uniform thickness along a length of a sleeve.

FIG. 4 is a cross-sectional side view of another exemplary sleeve valve catheter 44 that has a non-uniform thickness along a length of sleeve 30. Sleeve valve catheter 44 conforms substantially to sleeve valve catheter 28 illustrated in FIG. 2, but a thickness of sleeve 30 near distal end 18 is thinner than a thickness of sleeve 30 toward proximal end 16. The varying thickness along the length of sleeve 30 causes sleeve 30 to be more compliant toward distal end 18. In this manner, the pressure differential necessary to open sleeve 30 toward distal end 18 is decreased, in turn, causing sleeve valve 29 to more likely infuse fluids toward distal end 18. In an alternate embodiment, the varying thickness along the length of sleeve 30 is in the other direction, i.e., the thickness of sleeve 30 near proximal end 16 is thinner than a thickness of sleeve 30 toward distal end 18.

Figure 5:
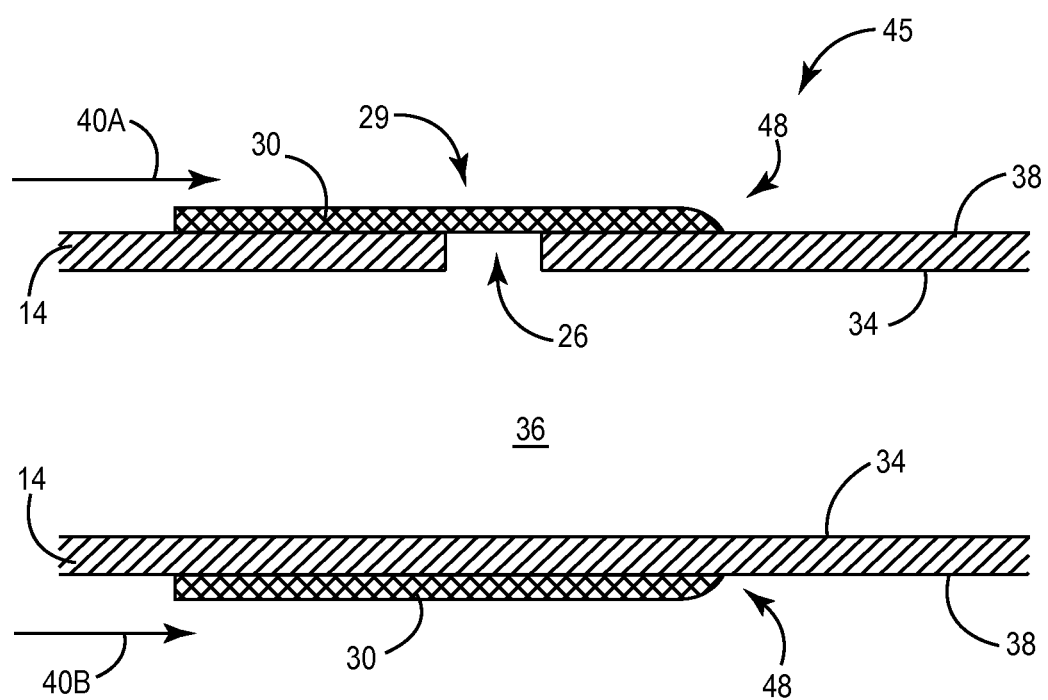
FIG. 5 is a cross-sectional side view illustrating another exemplary sleeve valve catheter that comprises a sleeve with a tapered edge.

FIG. 5 is a cross-sectional side view of another exemplary sleeve valve catheter 45 that comprises a sleeve 30 with a tapered edge 48 to reduce the likelihood of occlusion. Sleeve valve catheter 45 conforms substantially to sleeve valve catheter 28 illustrated in FIG. 2, but tapered edge 48 is shaped differently from tapered edge 32 of FIG. 2. Tapered edge 48 is a curved taper instead of a constant negative slope taper. More particularly, the curved taper of tapered edge 48 takes a convex shape. However, the tapered edge of the sleeve valve catheters may take any shape.

Figure 6:
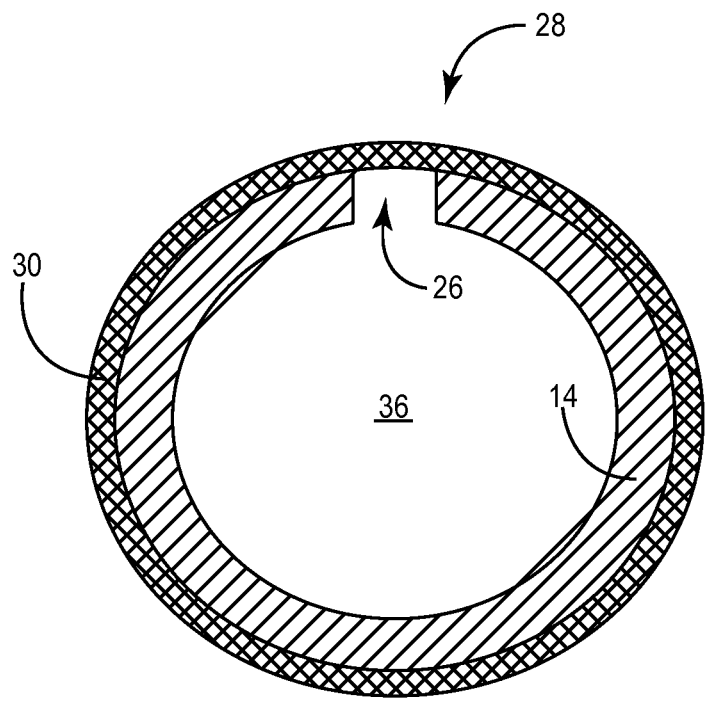
FIG. 6 is a cross-sectional end view illustrating the sleeve valve catheter of FIG. 2.

FIG. 6 is a cross-sectional end view of sleeve valve catheter 28 of FIG. 2 from C to C'. Sleeve valve catheter 28 includes a catheter body 14 that defines a lumen 36. Sleeve valve catheter 28 further includes at least one exit port 26. A sleeve 30 completely encircles catheter body 14 adjacent exit port 26 and covers exit port 26. As shown in the example of FIG. 6, an inner diameter of sleeve 30 is substantially the same as an outer diameter of catheter body 14. In other embodiments, the unstretched inner diameter of sleeve 30 is slightly smaller than the outer diameter of catheter body 14 in order to obtain a tighter fit. The tighter fit of sleeve 30 around the portion of catheter body 14 adjacent exit port 26 forms a stronger seal while sleeve valve catheter 28 and, more particularly, sleeve valve 29 is in a closed state. The seal reduces the likelihood of blood ingression, which may lead to occlusion. Although in the example of FIG. 6 sleeve valve catheter 28 has a circular shape, sleeve valve catheter 28 may be geometrically formed to take any shape.

Figure 7:
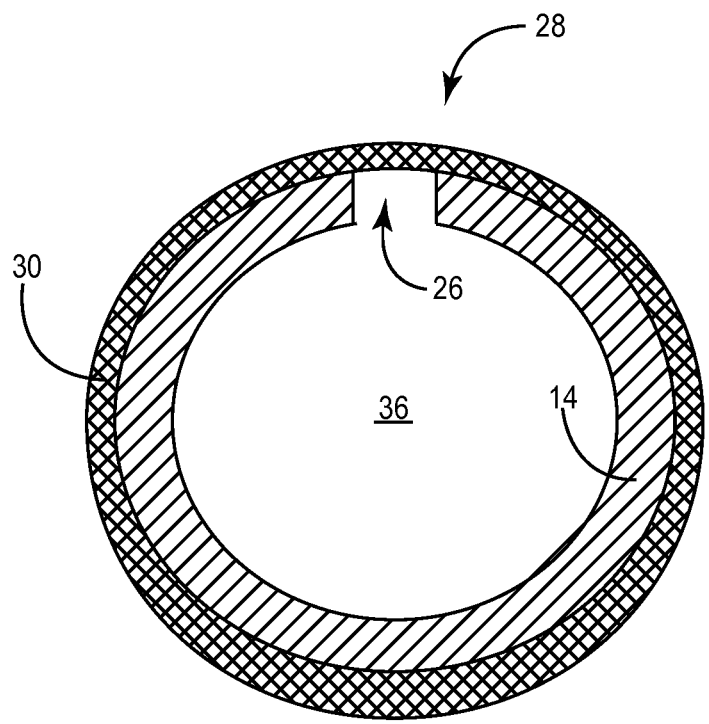
FIG. 7 is a cross-sectional end view of a sleeve valve catheter with a non-uniform thickness.

In the example illustrated in FIG. 6, sleeve 30 has a uniform thickness, i.e., the thickness of sleeve 30 remains the same around the entire circumference of catheter body 14. However, in an alternate embodiment, sleeve 30 is formed with a non-uniform thickness around the circumference of the catheter body, as illustrated in FIG. 7. In the example illustrated in FIG. 6, the thickness of sleeve 30 is less than the thickness of catheter body 14 in order for sleeve 30 to be more compliant than catheter body 14. As mentioned above, molding sleeve 30 using LSR allows sleeve 30 to be thinner and more uniform than when sleeve 30 is formed via conventional molding or other shaping techniques. In addition, LSR molding permits sleeve 30 to be molded with nonuniformities, if desired, such as reduced thicknesses in particular areas.

In the example illustrated in FIG. 6, sleeve valve catheter 28 includes a single exit port 26. However, in alternate embodiments, sleeve valve catheter 28 includes multiple exit ports covered by sleeve 30 and circumferentially displaced relative to one another around the circumference of catheter body 14 to reduce the pressure differential needed to expand sleeve 30 to open sleeve valve catheter 28.

FIG. 7 is a cross-sectional end view of a sleeve valve catheter 49 with a non-uniform thickness about the circumference of catheter body 14. Sleeve valve catheter 49 conforms substantially to sleeve valve catheter 28 illustrated in FIG. 6, but sleeve 51 has a non-uniform thickness. Specifically, the thickness of sleeve 51 proximate exit port 26 is less than the thickness of a major portion of sleeve 51. The reduced thickness of sleeve 51 proximate exit port 26 makes sleeve 51 proximate exit port 26 more resilient and decreases the pressure differential needed to separate sleeve 51 from catheter body 14. In this manner, the thickness of sleeve 51 may be adjusted in order to adjust the pressure differential required to expand and open sleeve 51.

Figure 8:
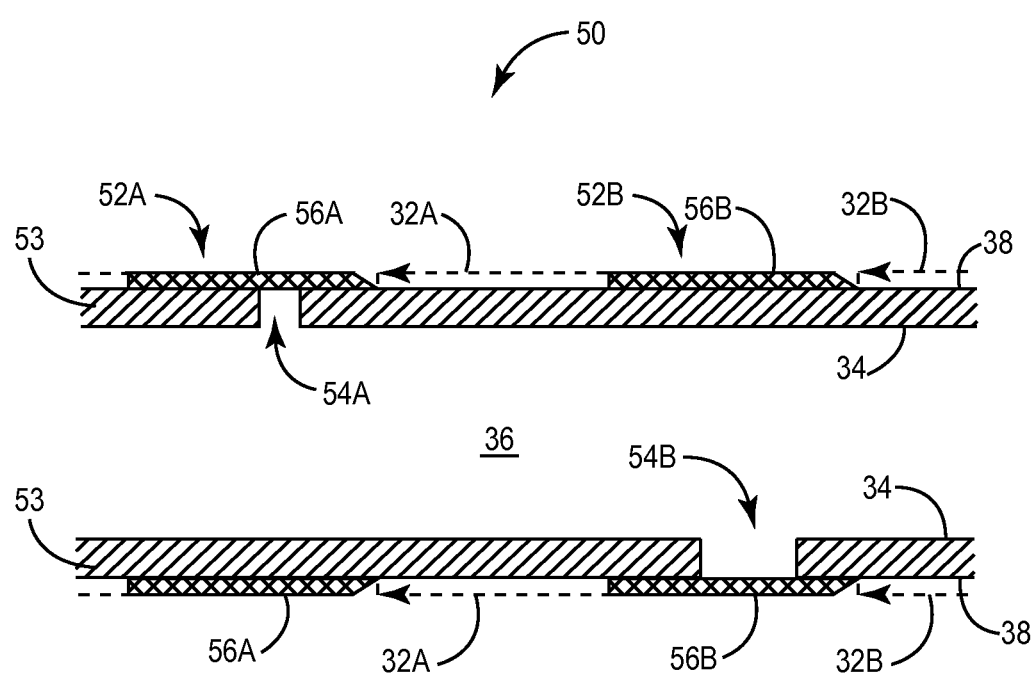
FIG. 8 is a cross-sectional side view illustrating another exemplary sleeve valve catheter that comprises a plurality of sleeve valves with tapered edges.

FIG. 8 is a cross-sectional side view of another exemplary sleeve valve catheter 50 that comprises a plurality of sleeve valves 52A-52B ("sleeve valves 52") with tapered edges 32A-32B ("tapered edges 32") to reduce the likelihood of occlusion.

Sleeve valve catheter 50 comprises a catheter body 53 that includes an interior surface 34 defining a lumen 36 and an exterior surface 38 exposed to an environment within a vessel. Sleeve valve catheter 50 further includes exit ports 54A-54B ("exit ports 54") along catheter body 53 through which material exits lumen 36. Exit ports 54 may be circular, oval, square or any other geometric shape. Sleeves 56A-56B ("sleeves 56") surround a portion of exterior surface 38 adjacent respective exit ports 54 and cover exit ports 54. Although sleeve valve catheter 50 of FIG. 8 only includes sleeve valves 52A and 52B, sleeve valve catheter 50 may include any number of sleeve valves 52.

As illustrated in FIG. 8, exit ports 54 are longitudinally displaced relative to one another along a length of catheter body 53 and exit port 54A is located farther from distal end 16 than exit port 54B. As further illustrated in FIG. 8, exit ports 54 are circumferentially displaced relative to one another along the length of catheter body 54. In the example cross section of FIG. 8, exit port 54A resides on a top circumferential portion and exit port 54B resides on a bottom circumferential portion of catheter body 53. In this manner, exit ports 54 reside on opposite sides of catheter body 53. In an alternate embodiment, exit ports 54 are both on a top portion of catheter body 53. The longitudinal and circumferential displacement of exit ports 54 provides redundancy in case one of exit ports 54 becomes occluded.

According to embodiments of the present invention, sleeve valves 52 are constructed to allow material to exit lumen 36 at different pressure levels. The pressure differential at which sleeve valves 52 allow material to exit lumen 36 are adjusted by selecting the size of exit ports 54, the length and thickness of sleeves 56, the compliance of sleeves 56, the number of exit ports associated with each of sleeves 56 or a combination thereof. For example, exit port 54B is larger than exit port 54A in order to reduce the pressure level at which slit valve 52B will open. In this manner, sleeve valve catheter 50 may be designed such that sleeve valve 52A functions as a surrogate valve for sleeve valve 52B. In other words, sleeve valve 52A allows material to exit lumen 36 only when sleeve valve 52B becomes occluded. For example, sleeve valve 52B may allow material to exit lumen 36 at a lower pressure differential than sleeve valve 52A. When sleeve valve 52B becomes occluded, material no longer exits lumen 36, in turn, causing the pressure level within lumen 36 to increase. The pressure level within lumen 36 continues to increase until the pressure level exceeds a threshold pressure differential of sleeve valve 52A. In this manner, when one of exit ports 54 becomes occluded, catheter 50 may remain implanted instead of being replaced.

Although in the example illustrated in FIG. 8 tapers 32 of sleeves 56 are linear, the tapers of sleeves 56 may be curved tapers that have a convex or concave shape. Further, the tapers of sleeves 56 may be a combination of different shaped tapers.

FIG. 9 is a cross-sectional side view of an exemplary sleeve valve catheter 60 that includes a sleeve 64 having substantially the same outer diameter as catheter body 62 to reduce the likelihood of occlusion of catheter 60. FIG. 9(A) illustrates sleeve valve catheter 60 in a closed state. FIG. 9(B) illustrates sleeve valve catheter 60 in an open state.

Sleeve valve catheter 60 comprises a catheter body 62 that includes an interior surface 66 defining a lumen 68 and an exterior surface 70 exposed to an environment within a vessel 12. Exterior surface 70 includes at least one recessed area 72 to receive sleeve 64. Sleeve valve catheter 60 further includes at least one exit port 74 along catheter body 62 through which material may exit lumen 68. As illustrated in FIG. 9, exit port 74 is formed within recessed area 72 of catheter body 62. Sleeve 64 surrounds exterior surface 70 of recessed area 72 adjacent exit port 74 and covers exit port 74. Sleeve 64 and exit port 74 together comprise a sleeve valve 76.

According to one embodiment, an inner diameter of sleeve 64 is substantially the same as an outer diameter of recessed area 72 of catheter body 62; in an alternate embodiment, the inner diameter of sleeve 64 is slightly smaller than the outer diameter of recessed area 72 in order to fit tightly. As illustrated in FIG. 9, the outer diameter of sleeve 64 is substantially the same as an outer diameter of a non-recessed portion of catheter body 62. In this manner, the exterior surface of sleeve 64 is substantially flush with exterior surface 70 of catheter body 62, which reduces the likelihood of thrombus formation from turbulence and/or stagnancy in the blood flow.

In order to form sleeve valve 76, a solvent that causes sleeve 64 to expand may be applied to sleeve 64 in order to fit sleeve 64 over non-recessed portions of catheter body 62. After sleeve 64 is in place, the solvent begins to evaporate, in turn, causing sleeve 64 to contract to the original size. Examples of solvents include isopropyl alcohol and heptane.

In the example illustrated in FIG. 9(B), sleeve valve 76 is in an open state. Sleeve valve 76 transforms from the closed state to the open state in response to an increased pressure level within lumen 68. More particularly, as the pressure of a material within lumen 68 increases, the material begins to attempt to exit lumen 68 via exit port 74. As the pressure of the fluid attempting to exit lumen 68 via exit port 74 increases, sleeve 64 begins to expand. Sleeve 76 continues to expand, in turn, separating sleeve 64 from exterior surface 70 of recessed area 72. When the pressure differential between inside catheter body 62 and outside catheter body 62 is large enough, sleeve 64 separates from exterior surface 70 and puts lumen 68 in fluid communication with the blood flow through vessel 12. In this manner, sleeve valve catheter 60 opens to infuse nutrients or therapeutic agents into the body of the patient.

As described above for sleeves with a tapered edge, sleeve 64 is constructed of an elastic material such as silicone. According to one embodiment of the present invention, sleeve 64 is molded using LSR molding techniques to achieve a thinner, more uniform sleeve than may be achieved via conventional shaping techniques. Catheter body 62 is constructed such that sleeve 64 is more compliant than catheter body 62. In one embodiment according to the present invention, catheter body 62 is constructed of a non-compliant polymer such as polyurethane, fluoropolymer, polyimide, polyamide, polyethylene, or polypropylene. According to an alternate embodiment, catheter body 62 is constructed of silicone. In the case in which both catheter body 62 and sleeve 64 are constructed of silicone, catheter body 62 may be thicker than sleeve 64 so that the compliance of sleeve 64 is greater. Further, in one embodiment, a material, such as graphite or talc, is applied at an interface between sleeve 64 and body 62 in order to prevent blocking between body 62 and sleeve 64 due to crosslinking.

Figure 10A:
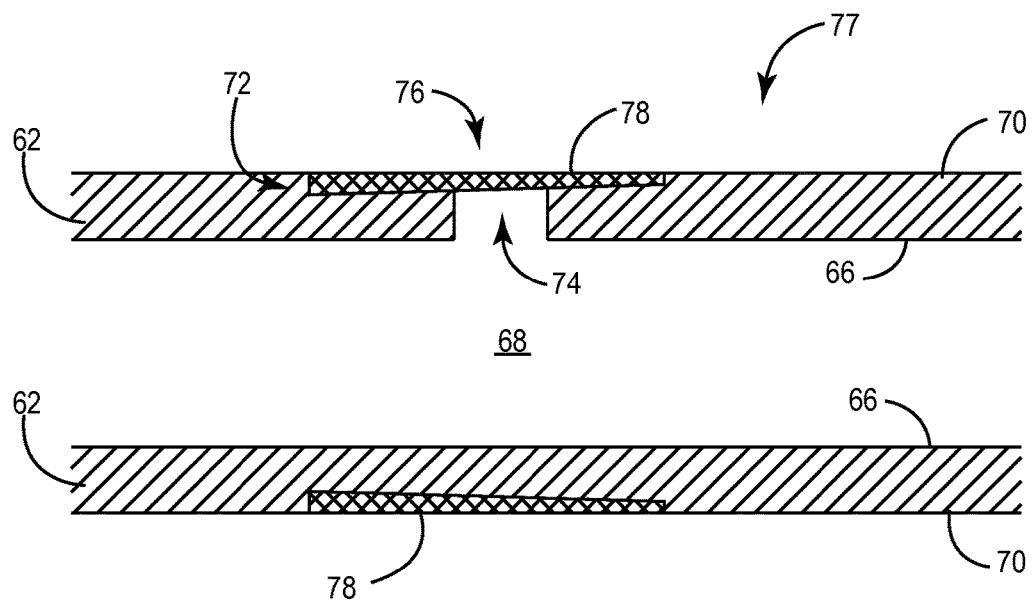
FIGS. 10A and 10B are cross-sectional side views of other exemplary sleeve valve catheters that include a sleeve having substantially the same outer diameter as catheter body.
Figure 10B:
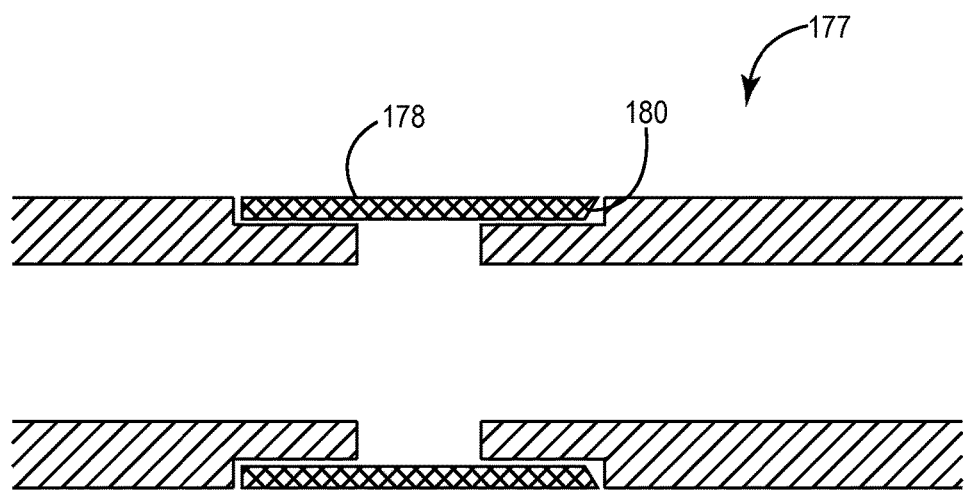

FIG. 10A is a cross-sectional side view of another exemplary sleeve valve catheter 77 that includes a sleeve 78 having substantially the same outer diameter as catheter body 62 to reduce the likelihood of occlusion of catheter 77. Sleeve valve catheter 77 conforms substantially to sleeve valve catheter 60 illustrated in FIG. 9, but sleeve 78 has a non-uniform thickness. More specifically, a thickness of sleeve 78 near distal end 18 is thinner than a thickness of sleeve 78 toward proximal end 16, providing sleeve 78 with a tapered diametric profile. The varying thickness along the length of sleeve 78 causes sleeve 78 to be more compliant toward distal end 18. In this manner, the pressure differential necessary to open sleeve valve 76 toward distal end 18 is decreased, in turn, causing sleeve valve 76 to more likely infuse fluids toward distal end 18. In an alternate embodiment, the varying thickness along the length of sleeve 78 is in the other direction, i.e., the thickness of sleeve 78 near proximal end 16 is thinner than a thickness of sleeve 78 toward distal end 18. FIG. 10B is a cross-sectional side view of yet another exemplary sleeve valve catheter 177. As illustrated in FIG. 10B sleeve 178 includes an internal tapered edge 180.

Figure 11:
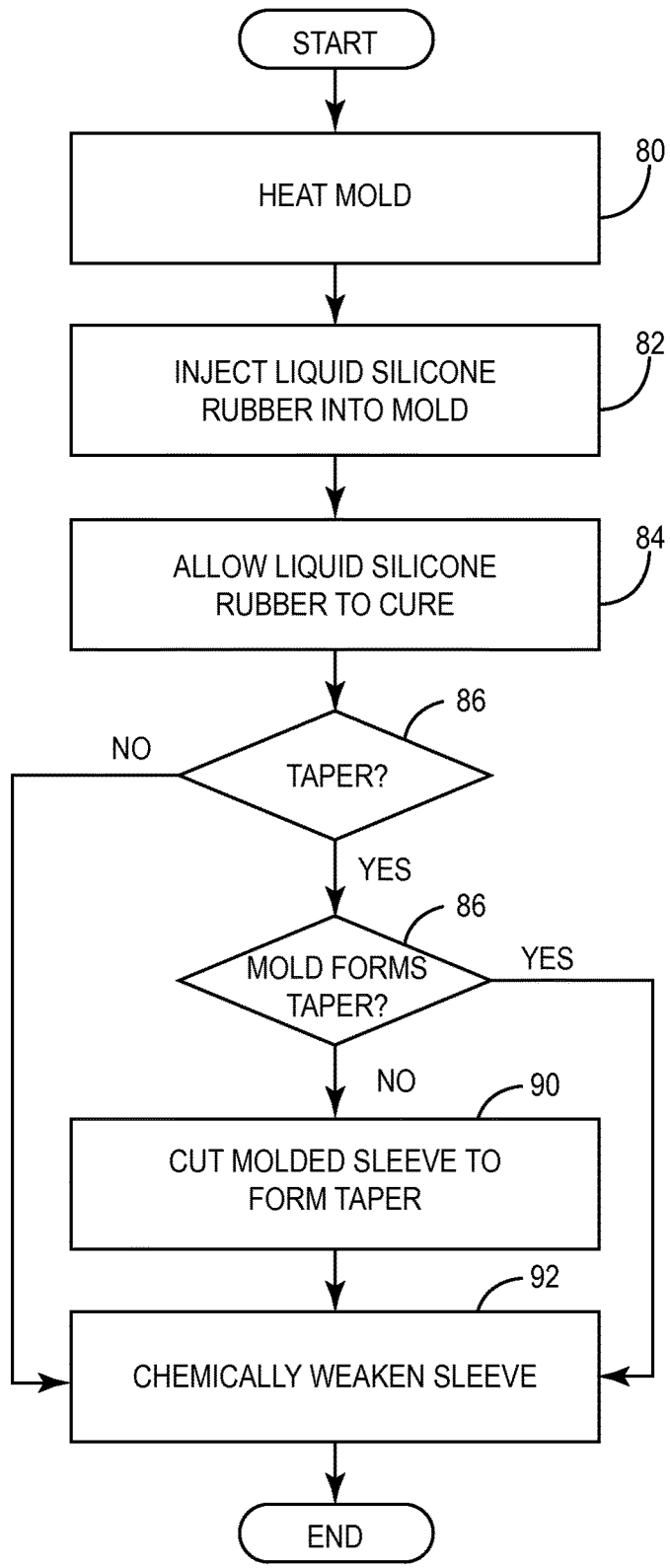
FIG. 11 is a flow diagram illustrating a method of manufacturing a sleeve of a sleeve valve catheter.

FIG. 11 is a flow diagram illustrating a method of manufacturing sleeves of sleeve valve catheters, such as sleeve 24 of FIG. 1. Initially, a mold having an inner cavity that is shaped like a sleeve of a sleeve valve catheter is heated (80). The mold may be heated while the mold is in a closed position. The mold is shaped to form a sleeve that has a uniform thickness or the mold is shaped to form a sleeve that has a non-uniform thickness. The mold may also be shaped to attain a sleeve with tapered edges.

Next, LSR is injected into the heated mold and allowed to cure (82, 84). The LSR injected into the mold has a lower viscosity prior to curing than does conventional silicones, such as gum stock silicone. The lower viscosity provides the LSR the ability to flow and cure with a thickness that is much thinner than attainable via conventional molding techniques such as hot and cold transfer molding or injection molding. According to one embodiment of the present invention, the LSR injected into the mold has a durometer between approximately 30 and approximately 70 on a shore A scale. However, the durometer value of the LSR may vary depending on the application of the sleeve valve catheter. According to the present invention, thicknesses of alternate embodiments of sleeves formed from injection-molded LSR range from approximately 0.002 inch to approximately 0.010 inch. When a taper is desired at one or more edges of the sleeve and the mold is not shaped to form the tapered edge, the cured LSR sleeve is cut to form the taper (86, 88, 90).

According to one embodiment of the present invention, the sleeve, whether tapered or not, is chemically weakened to increase the compliance of the sleeve (92). The sleeve may, for example, be chemically weakened by adding silicone oil to decrease the amount of silica in the LSR injected into the mold. Alternatively, a lower durometer LSR may be used. The increased compliance of the sleeve lowers the pressure differential needed to open the sleeve valve.

Figure 12:
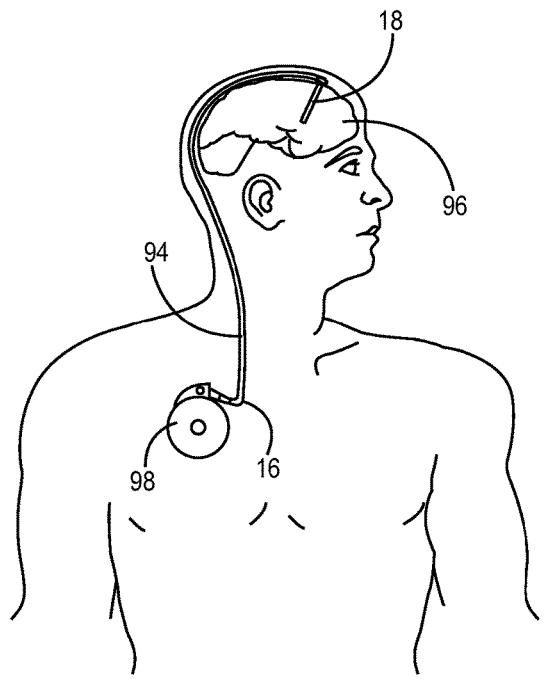
FIG. 12 is a schematic diagram illustrating an implanted catheter including a sleeve valve according to one embodiment of the present invention.

FIG. 12 is a schematic diagram illustrating an implanted catheter including a sleeve valve according to one embodiment of the present invention. As illustrated in FIG. 12, a sleeve valve catheter 94 includes a distal end 18 implanted within a brain 96 and a proximal end 16 coupled to an implanted pump 98. Catheter 94 further includes at least one sleeve valve, conforming to any of the embodiments described herein, near distal end 18 for delivery of therapeutic agents or nutrients from pump 98 to brain 96. One embodiment of catheter 94 is further described in conjunction with FIG. 14.

Figure 13:
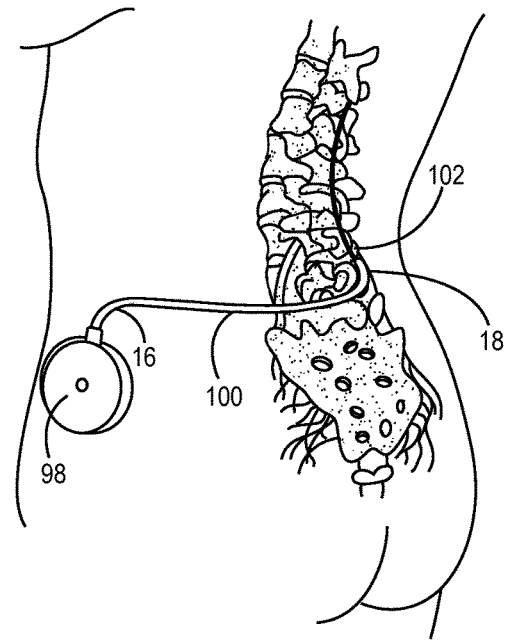
FIG. 13 is a schematic diagram illustrating an implanted catheter including a sleeve valve according to another embodiment of the present invention.

FIG. 13 is a schematic diagram illustrating an implanted catheter including a sleeve valve according to another embodiment of the present invention. As illustrated in FIG. 13, a sleeve valve catheter 100 includes a distal end 18 implanted within a spine 102 and a proximal end 16 coupled to an implanted pump 98. Catheter 100 further includes at least one sleeve valve, conforming to any of the embodiments described herein, near distal end 18 for delivery of therapeutic agents or nutrients from pump 98 to spine 102.

Figure 14:
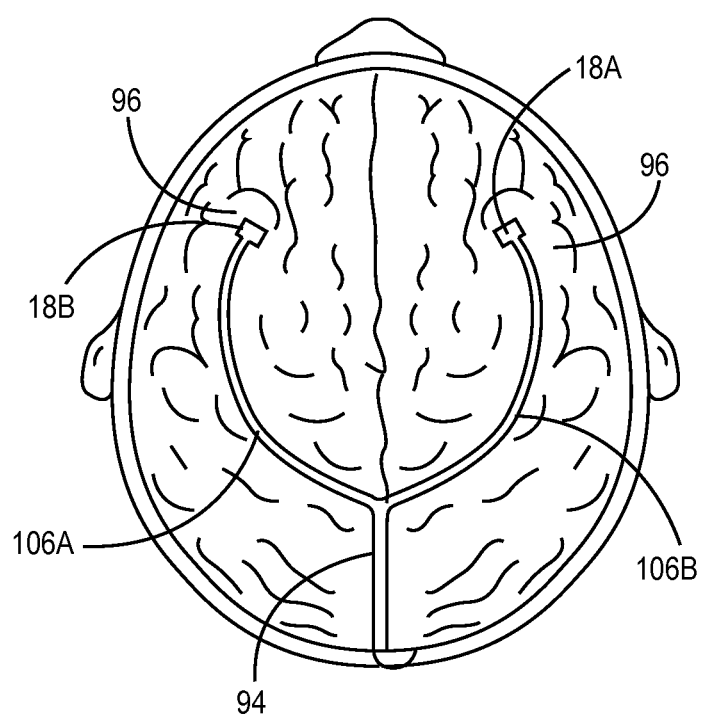
FIG. 14 is a schematic diagram illustrating a distal end of the implanted catheter of FIG. 12.

FIG. 14 is a schematic diagram illustrating a distal end of the implanted catheter of FIG. 12. As illustrated in FIG. 14, distal end 18 of sleeve valve catheter 94 includes branches 106A and 106B, each branch including at least one sleeve valve, conforming to any of the embodiments described herein.

EXAMPLES

Sleeve valve catheter patency was evaluated for small volume, intermittent, fluid delivery for twelve weeks in a canine model. Results for a first sleeve valve catheter, identified herein as #9134, and a second sleeve valve catheter, identified herein as #9248, are presented in Table 1 and Table 2, respectively.

Catheter bodies for the two sleeve valve catheters were fabricated from extruded NuSil Med4719 silicone tubing having a durometer of approximately 55 on a Shore A scale, an ID of approximately 0.040 inch, and an OD of approximately 0.080 inch. For each catheter, a sleeve was fitted over an exit port formed in the catheter body in proximity to a distal end of the catheter. The sleeves, including tapered edges and having a wall thickness of approximately 0.0025 inch, were fabricated from Dow Corning G7-4850 molded liquid silicone rubber having a durometer of approximately 50 on a Shore A scale. A graphite material, Graphite Micro #250 available from Asbury Graphite Mills Inc., was spread between an internal surface of the sleeve and the catheter body, in proximity to the exit port, to reduce blocking between the sleeve and the catheter body.

Pressure waveforms were recorded during bolus delivery of saline at weeks 0, 1, 2, 3, 5, 7, 9, and 12. Each bolus had a volume of approximately 0.1 milliliter and was delivered at an infusion rate of approximately 0.05 milliliter per minute. During the fluid injection, intra-catheter pressures were recorded.

TABLE 1

Pressures for sleeve valve of # 9134—implanted at a junction of a jugular vein and a superior vena cava.

| | PRESSURE (mmHg) | | | | | | | |
|---|---|---|---|---|---|---|---|---|
| Weeks | 0 | 1 | 2 | 3 | 5 | 7 | 9 | 12 |
| Steady State | 76 | 69 | 67 | NA | 61 | 75 | 75 | 73 |
| Maximum | 88 | 93 | 87 | NA | 73 | 80 | 84 | 78 |

TABLE 2

Pressures for sleeve valve of #9248—implanted at a junction of a superior vena cava and an atrium

| | PRESSURE (mmHg) | | | | | | | |
|---|---|---|---|---|---|---|---|---|
| Weeks | 0 | 1 | 2 | 3 | 5 | 7 | 9 | 12 |
| Steady State | 62 | 94 | 77 | 63 | 65 | 62 | 67 | 80 |
| Maximum | 63 | 98 | 85 | 80 | 71 | 85 | 87 | 247 |

Figure 15:
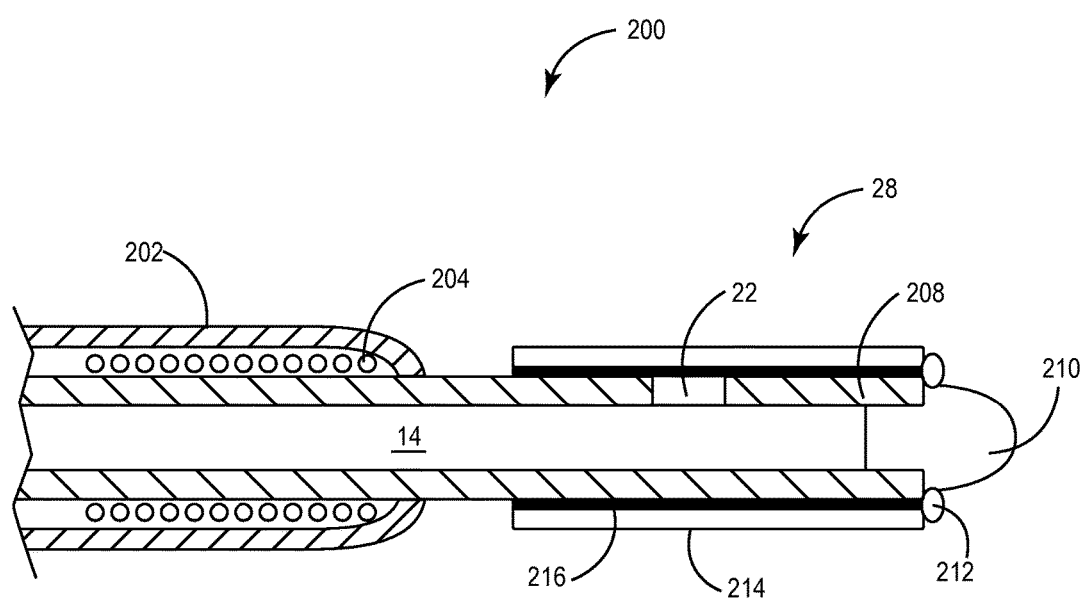
FIG. 15 is a schematic diagram illustrating a sleeve valve catheter.

FIG. 15 depicts medical device 200. Medical device 200 includes a coil 204 reinforced catheter 202, a catheter body 14, a sleeve valve catheter 228, and catheter tip 210. Catheter 202 is proximal to sleeve valve catheter 228. Catheter 202 includes a coil 204 to prevent kinking and collapse of a lumen associated with catheter body 14.

Sleeve valve 214 surrounds catheter body 208. In this embodiment, sleeve valve 28 includes an anti-blocking interface 216 disposed between sleeve 214 and tubing 208. Anti-blocking interface 216 comprises graphite, talc or other suitable material. In one embodiment, anti-blocking interface 216 extends the full length of sleeve 214. In another embodiment, anti-blocking interface 216 covers only a portion of sleeve 214. An adhesive bond 212 is coupled to sleeve 214, blocking interface 216, and tubing 208. Adhesive bond 212 essentially mechanically connects together sleeve 214, blocking interface 216, and tubing 208. Exemplary adhesive bond 212 includes silicone medical adhesive. Catheter tip 210 extends distally from sleeve 214. Catheter tip 210 comprises a radiopaque material such as barium, tantalum, or platinum filled silicone.

Various embodiments along with examples of the invention have been described. Various modifications may be made without departing from the scope of the claims. The techniques of the invention may, for example, be applied to a catheter that has a sleeve valve and a slit valve. Further, the techniques of the invention may be applied to a multi-lumen catheter. For example, a first lumen within the multi-lumen catheter may be associated with a first sleeve valve and a second lumen within the multi-lumen catheter may be associated with a second sleeve valve. The sleeve valves associated with the first and second lumens may correspond only to their respective lumens such that the fluids of the lumens do not interact with one another within the catheter. These and other embodiments are within the scope of the following claims.

The invention claimed is:

1. A medical device comprising:
   a catheter body including an interior surface defining a lumen and an exterior surface of silicone rubber;
   an exit port formed within the catheter body to allow material to exit the lumen of the catheter body;
   a pressure responsive sleeve of silicone rubber fitting located in an interference fit around the exterior surface having and covering the exit port, expandable from a closed position to an open position; and
   an anti-blocking agent between the sleeve and the catheter body, proximate the exit port.

2. The medical device of claim 1, wherein the anti-blocking agent comprises graphite.

3. The medical device of claim 1, wherein the anti-blocking agent comprises talc.

4. The medical device of claim 1, wherein the anti-blocking agent extends from about an entire length of the sleeve to about half the sleeve length.

5. A medical device comprising:
   a catheter body including an interior surface defining a lumen and an exterior surface of silicone rubber;
   an exit port formed in the catheter body to allow material to exit the lumen of the catheter body;
   a pressure responsive sleeve formed from molded liquid silicone rubber having a wall thickness between approximately 0.002 inch and approximately 0.010 inch wherein the sleeve surrounds a portion of the exterior surface of the catheter body and covers the exit port; and
   an anti-blocking agent between the sleeve and the catheter body.

6. The medical device of claim 5, wherein the molded liquid silicone rubber has a durometer between approximately 30 and approximately 70 on a shore A scale.

7. The medical device of claim 5, wherein the anti-blocking agent comprises graphite.

8. The medical device of claim 5, wherein the anti-blocking agent comprises talc.

9. The medical device of claim 5, wherein the anti-blocking agent extends from about an entire length of the sleeve to about half the sleeve length.

* * * * *